US008945641B2

(12) United States Patent
Terragno et al.

(10) Patent No.: US 8,945,641 B2
(45) Date of Patent: Feb. 3, 2015

(54) USE OF GUM ARABIC FOR IMPROVING THE GROWTH AND SURVIVAL OF BIFIDOBACTERIA

(75) Inventors: Luc Terragno, Meudon (FR); François Debru, Versailles (FR); Stéphane Herve, Sceaux (FR); Philippe Teissier, Palaiseau (FR)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 12/443,883

(22) PCT Filed: Oct. 1, 2007

(86) PCT No.: PCT/FR2007/001598
§ 371 (c)(1),
(2), (4) Date: Jun. 3, 2009

(87) PCT Pub. No.: WO2008/040872
PCT Pub. Date: Apr. 10, 2008

(65) Prior Publication Data
US 2010/0272854 A1   Oct. 28, 2010

(30) Foreign Application Priority Data
Oct. 2, 2006 (FR) .................................. 06 08613

(51) Int. Cl.
*A23L 3/3571* (2006.01)
*A23C 9/123* (2006.01)
*A23C 9/13* (2006.01)
*A23C 9/137* (2006.01)
*A23L 1/053* (2006.01)
*C12N 1/20* (2006.01)
*C12N 1/38* (2006.01)

(52) U.S. Cl.
CPC ............. *A23C 9/1234* (2013.01); *A23C 9/1322* (2013.01); *A23C 9/137* (2013.01); *A23L 1/053* (2013.01); *C12N 1/20* (2013.01); *C12N 1/38* (2013.01)
USPC ................................................ 426/8; 426/61

(58) Field of Classification Search
CPC .... A23C 9/1234; A23C 9/1322; A23C 9/137; A23L 1/053; C12N 1/20; C12N 1/38
USPC ....................................................... 426/8, 61
See application file for complete search history.

(56) References Cited

U.S. PATENT DOCUMENTS

| 5,230,912 A * | 7/1993 | Yajima et al. ................... 426/43 |
| 5,952,021 A | 9/1999 | Santus | |
| 6,093,425 A * | 7/2000 | Kamarei .......................... 426/72 |
| 2005/0233049 A1 | 10/2005 | Gutknecht et al. | |
| 2006/0057131 A1 | 3/2006 | Simard et al. | |
| 2008/0181986 A1 | 7/2008 | Terragno et al. | |
| 2009/0324776 A1 | 12/2009 | Marchal et al. | |

FOREIGN PATENT DOCUMENTS

| FR | 2 815 823 A1 | 5/2002 |
| WO | WO 99/04649 | 2/1999 |

OTHER PUBLICATIONS

FR-2-815-823-Machine Translation.*
KR-2005-007206-English Abstract.*
Akalin, A. S. et al. 2007. Effects of Fructooligosaccharides and whey protein conentrate on the viability of starter culture in reduced-fat probiotic yogurt during storage. J. Food. Sci. 72: M222-M227.*
International Search Report and Written Opinion for PCT/FR2007/001598 filed Oct. 1, 2007.
Crociani F et al: "Degradation of Complex Carbohydrates by Bifidobacterium SPP"; International Journal of Food Microbiology; Elsevier Science Publishers; Amsterdam, NL; vol. 24, 1994; pp. 199-210; XP001009939.
Wen-Chian Lian et al: "Survival of bifidobacteria after spray-drying"; International Journal of Food Microbiology; vol. 74, No. ½, 2002, pp. 79-86, XP009085030.
Lian Wen-Chian et al: "Viability of microencapsulated bifidobacteria in simulated gastric juice and bile solution"; International Journal of Food Microbiology; vol. 86, No. 3, Sep. 15, 2003; pp. 293-301, XP002437472.
Hsiao Hung-Chi et al: "Effect of packaging conditions and temperature on viability of microencapsulated bifidobacteria during storage"; Journal of the Science of Food and Agriculture; [Online]; vol. 84, No. 2; Jan. 5, 2004; pp. 134-139, XP002347473.
Michel C et al: "In vitro prebiotic effects of Acacia gums onto the human intestinal microbiota depends on both botanical origin and environmental pH"; Anaerobe, [Online]; vol. 4, No. 6, Dec. 1998; pp. 257-266, XP002437632.

* cited by examiner

*Primary Examiner* — Hamid R Badr
(74) *Attorney, Agent, or Firm* — Alston & Bird LLP

(57) ABSTRACT

The invention relates to the use of *acacia* gum (or gum Arabic) possibly in combination with sulphur-containing amino acids, for improving the growth and survival of bifidobacteria which are part of the manufacture of fermented food products, in particular, of fermented milk products.

13 Claims, 6 Drawing Sheets

USE OF GUM ARABIC FOR IMPROVING THE GROWTH AND SURVIVAL OF BIFIDOBACTERIA

CROSS REFERENCE TO RELATED APPLICATIONS

This application is a national stage application filed under 35 U.S.C. 371 of International Application No. PCT/FR2007/001598, filed Oct. 1, 2007, which claims priority to French Application No. 06 08613, filed Oct. 2, 2006.

FIELD AND BACKGROUND OF THE INVENTION

The invention relates to the use of *acacia* gum (or gum arabic), alone or in combination with a sulfur-containing amino acid, for improving the growth and survival of bifidobacteria entering into the manufacture of fermented food products.

Bifidobacteria are one of the most commonly used probiotic microorganisms nowadays in the manufacture of various food products, and in particular of fermented dairy products.

Probiotics are defined as "live microorganisms which, when consumed in adequate amounts, confer a health benefit on the host" (report of the mixed consultation of FAO/WHO experts on the evaluation of the health and nutritional properties of probiotics in foods, 2001). This definition implies that to exert its beneficial effect, the relevant microorganism should be present in a sufficient amount in the ready-to-consume product. It is generally considered that this amount should be at least equal to $10^7$ cfu/ml. Maintaining the viability of probiotic bacteria during manufacture, packaging and storage of food products containing them therefore constitutes an essential component of the quality of these products.

The species of bifidobacteria most widely used in the food sector are *Bifidobacterium adolescentis, B. bifidum, B. breve, B. longum, B. animalis* and *B. infantis*.

In the context of the manufacture of fermented food products, the bifidobacteria may be used alone; however, they are most often, for organoleptic and/or technological reasons, combined with other lactic acid bacteria. They are in particular frequently combined with yogurt ferments (*L. Bulgaricus* and *S. thermophilus*). They may be added to already fermented products or, more commonly, mixed with other lactic acid bacteria, during inoculation of the substrate to be fermented.

Under the conditions for carrying out the manufacture of food products, the growth of bifidobacteria is frequently slow; in addition, at the end of the fermentation, it is often difficult to maintain a sufficient bifidobacteria population during the whole period of storage of the product up to its consumption. These problems may be increased if the bifidobacteria are combined with other lactic acid bacteria. Because of the low competitiveness of bifidobacteria in mixed culture, they often grow more slowly in the presence of other lactic ferments than when they are cultured alone; otherwise, their survival during storage of the fermented product is generally poorer, in particular, especially since some other lactic acid bacteria continue to produce, amongst others, lactic acid. This phenomenon, known as post-acidification, affects the viability of the bifidobacteria present in the same product.

In this context, it seems desirable to stimulate the growth and increase the viability of bifidobacteria, and preferably, to do this while inducing little or no effect (positive or negative) on the growth and viability of the lactic acid bacteria with which these bifidobacteria are combined.

The inventors have discovered that the use of gum arabic during the manufacture of fermented products made it possible to obtain these results.

Gum arabic is produced by exudation of wounds of the trunks or branches of certain species of *acacia*. It is a highly branched, high-molecular-weight, water-soluble polysaccharide. The gum arabic used as food additive (E414) is obtained exclusively from *Acacia seyal* or *Acacia senegal*.

It has been proposed to use gum arabic to encapsulate probiotic bacteria (various bifidobacteria and *Lactobacillus paracasei*) in order to preserve them from heat and dehydration during drying, and to improve their viability, and their resistance to the gastric fluids and to bile (Lian et al. 2002; Lian et al. 2003; Hsiao et al. 2004; Desmond et al. 2002).

It has also been reported that the ingestion of gum arabic in humans, in an amount of 10 grams per day, made it possible to increase the *Bifidobacterium* and *Bacteroides* population in stools; more recently, a similar study has described an increase in the total population of lactic acid bacteria, and mainly of *Bifidobacterium* and *Lactobacillus*, after ingestion of 10 to 15 grams of gum arabic per day (Wyatt et al. 1986; Cherbut et al. 2003).

SUMMARY OF THE INVENTION

The inventors have observed that when gum arabic was added in vitro to a culture containing bifidobacteria, alone or with other lactic acid bacteria, it stimulated the growth of bifidobacteria during the fermentation, and increased their lifetime during the storage of the fermented product; on the other hand, it had little or no effect on the growth and viability of the other lactic acid bacteria when they were present. They furthermore observed that if cysteine was furthermore added, the specific effects of gum arabic on the bifidobacteria, in particular on their survival during preservation, was considerably increased.

The subject of the present invention is a method for increasing the viability of bifidobacteria during the preservation of a fermented fresh food product containing one or more strains of *Bifidobacterium*, characterized in that it comprises the addition of gum arabic to said food product before the end of its packaging.

According to a preferred embodiment of a method of the present invention, said food product additionally contains one or more strains of lactic acid bacteria other than *Bifidobacterium*.

According to another preferred embodiment of the present invention, said method additionally comprises the addition of at least one sulfur-containing amino acid (cysteine or methionine), preferably cysteine, to said food product before the end of its packaging.

"Fermented food product" is defined here as a product resulting from the fermentation of an appropriate food substrate by a ferment comprising lactic acid bacteria, and in which these lactic acid bacteria remain live. This product may also contain live lactic acid bacteria which did not participate in the fermentation, but were added at the end of it; it may also contain, where appropriate, microorganisms which can be used in food manufacture, other than lactic acid bacteria, for example *Acetobacter* or yeasts. The term "fresh" indicates that this product was not subjected, after fermentation, to any treatment such as lyophilization or drying. The fresh products are generally preserved by refrigeration.

The "end of packaging" defines the time of closure of the container in which the fermented product will be stored up to its consumption.

The appropriate food substrates for carrying out the present invention are all those which can be normally used for the production of fermented food products containing bifidobacteria.

They may be for example a milk substrate, which may be cow's, goat's, sheep's or horse's milk or milk from any other mammal whose milk can be used for human consumption; this milk may optionally have been subjected to various treatments which make it possible to control in particular its protein and fat composition (cream separation, ultrafiltration, concentration or dilution, addition of milk fractions, and the like); this may also be milk reconstituted from powdered milk or from milk fractions or from milk enriched with milk proteins and/or milk protein hydrolyzates.

This may also be a plant substrate, for example fruit or vegetable juice, soya milk, substrate based on cereals such as wheat, oats, corn and the like.

This may also be a mixture or mixtures of two or more of these substrates.

This may also be a substrate such as a fat-based filling.

When appropriate, said food substrate may be supplemented with various agents, such as texturing, taste-enhancing and flavoring agents, and the like.

Conventionally, before inoculation with the chosen bacteria, said substrate is heat-treated, for example at 90-95° C. for 5 to 10 minutes, in order to destroy potential bacterial contaminants.

The bifidobacteria strain(s) used for carrying out the present invention may be chosen from the abovementioned bifidobacteria species normally used for the preparation of food products. It is possible to combine bifidobacteria strains of different species. Preferred species are in particular *Bifidobacterium animalis*, and in particular the subspecies *Bifidobacterium animalis animalis* and *Bifidobacterium animalis lactis*. By way of example, there may be mentioned the *Bifidobacterium animalis lactis* CNCM I-2494 strain.

Other preferred species of bifidobacteria are *B. lactis* BB12 (CHR Hansen), *B. longum* BB536 (Morinaga), *B. breve* CNCM I-2219 (Danone), *B. breve* YIT 4014 (Yakult), *B. infantis* 35624 (Proctor & Gamble).

Other strains of lactic acid bacterium (bacteria) may also be chosen from those which are normally used for the preparation of food products.

Their choice depends on the type of fermented product which it is desired to obtain:

By way of nonlimiting example, there may be mentioned:

actobacilli such as *Lactobacillus acidophilus, Lactobacillus casei, Lactobacillus reteri, Lactobacillus helveticus, Lactobacillus plantarum* and the like;

yogurt ferments, namely *Streptococcus thermophilus* and *Lactobacillus delbrueckii* subsp. *bulgaricus*, which may, where appropriate, be combined with other species of *Lactobacillus;* kefir ferments, generally containing *Lactobacillus kefiri*, combined with bacteria of the genera *Leuconostoc, Lactococcus* and *Acetobacter*, and with yeasts of the genera *Kluyveromyces* and *Saccharomyces;* mesophilic bacteria used in particular for the manufacture of cheese, such as *Lactococcus cremoris, Lactococcus lactis, Lactococcus diacetylactis* and *Leuconostoc*.

It is also possible to use gum arabic from *Acacia senegal* or *Acacia seyal*, for example those respectively marketed by the company CNI under the names FIBREGUM® P and FIBREGUM® B or those marketed by the company Kerry Ingredients or by the company ALFRED L. WOLFF GmbH under the trademark Quick Gum®.

The sulfur-containing amino acid(s) will be preferably used in free form, according to the modalities described in the PCT application FR2006/001688, filed on 11 Jul. 2006 in the name of COMPAGNIE GERVAIS DANONE; it is also possible to use granules containing cysteine base, similar to those described in application FR 0606421 filed on 13 Jul. 2006 in the name of COMPAGNIE GERVAIS DANONE.

The quality of gum arabic in the final product (that is to say the fermented and packaged product) will be generally about 0.1 to about 3%, preferably about 0.2 to about 1% by weight. The quantity of sulfur-containing amino acid(s) in the final product may range from about 5 to about 50 mg/l; it will be generally from about 5 to about 20 mg/l, preferably from about 5 to about 15 mg/l, and advantageously from about 5 to about 10 mg/l.

The quantity of gum arabic used may be advantageously adjusted according to the desired protein content of the final product, and the addition or otherwise of sulfur-containing amino acid(s).

In the case of a product whose protein content is greater than or equal to 3.4%, the gum arabic may be used alone, preferably so as to obtain a quantity greater than or equal to 0.5% in the final product; if it is desired to obtain a quantity of gum arabic in the final product of less than 0.5%, it is preferable to also add the sulfur-containing amino acid(s).

In the case of a product whose protein content is less than 3.4%, it is generally preferable to use a combination of *acacia* gum and sulfur-containing amino acid(s), in particular in order to obtain an optimum effect on the survival of bifidobacteria.

In order to obtain the desired effect on the viability of bifidobacteria, the gum arabic, like the sulfur-containing amino acid(s), may be added, together or separately, and all at once or in several fractions, at any time during the manufacture of the product before the end of its packaging.

According to a preferred embodiment of the method of the present invention, it comprises a step of fermenting a food substrate by one or more *Bifidobacterium* strains, in combination or otherwise with one or more strains of one or more lactic acid bacteria other than *Bifidobacterium*.

In this case, in order to stimulate the growth of *Bifidobacterium*, the addition of at least a portion of the total quantity of gum arabic, and optionally of at least a portion of the total quantity of the sulfur-containing amino acid(s), is carried out before this fermentation. When the quantity of gum arabic envisaged in the final product is less than 0.5%, it is preferable that the entire gum arabic is added before fermentation; when the quantity of gum arabic envisaged in the final product is 0.5% to 1%, the quantity of gum arabic added before the fermentation preferably represents from 50 to 100% of the total quantity used; when the quantity of gum arabic envisaged in the final product is greater than 1%, the quantity of gum arabic added before the fermentation preferably represents from 20 to 100% of the total quantity used. Likewise, when the quantity of sulfur-containing amino acid(s) envisaged in the final product is from 5 to about 10 mg/l, the quantity of sulfur-containing amino acid(s) added before the fermentation preferably represents from 80 to 100% of the total quantity used; when the quantity of sulfur-containing amino acid(s) envisaged in the final product is greater than 10 mg/l, the quantity of sulfur-containing amino acid(s) added before the fermentation preferably represents from 20 to 100% of the total quantity used.

According to a particularly advantageous feature of this embodiment, at least a portion of the sulfur-containing amino acids used is added during the inoculation with bacteria, in the form of granules containing cysteine base as described in application FR 0606421, and containing at least one of the *Bifidobacterium* strains used.

A method in accordance with the invention may comprise several fermentation steps, carried out separately, using different combinations of lactic acid bacteria, and/or food substrates of a different nature. These fermentation steps are generally carried out in parallel, and their products are then mixed. It is possible for one of these separate fermentations to use a ferment which does not comprise bifidobacteria. In this case, it is not necessary to carry out the fermentation in the presence of gum arabic or of the gum arabic/sulfur-containing amino acid(s) combination; it is however possible to add, together or separately, the gum arabic, like the sulfur-containing amino acid(s), before, during or after the fermentation, so that they are present in the mixture of fermentation products.

In the context of the method of the invention, the quantity of bifidobacteria used for the inoculation of the food substrate is from about $10^6$ to about $2\times10^7$ CFU per ml of substrate. When the bifidobacteria are used to ferment a substrate together with other lactic acid bacteria, they generally represent from about 20 to about 75%, preferably from about 30 to about 50%, and in a particularly preferred manner from about 35 to about 40%, of the bacterial population present in the inoculum used.

The quantity of bifidobacteria in the final product, immediately after fermentation and packaging (that is to say within the 4 hours following the end of the fermentation), is at least $1\times10^8$, preferably of the order of $2\times10^8$ to $10^9$ CFU per ml of product.

When bifidobacteria are added to a product fermented by other lactic acid bacteria, the quantity added is also adjusted so as to also obtain a population of at least $1\times10^8$, preferably of the order of $2\times10^8$ to $10^9$ CFU per ml of product.

The method in accordance with the invention can be used for the manufacture of a wide variety of fermented fresh products, and may be used without modification, or after only minor modifications, of the customary modes of preparation of this type of product.

BRIEF DESCRIPTION OF THE DRAWINGS

FIG. 1 schematically represents the preparation of a fermented product of the stirred yogurt type;

FIG. 2 schematically represents the preparation of a fermented product of the drinking yogurt type;

FIG. 3 schematically represents the preparation of a fermented product containing yogurt ferments and kefir ferments;

FIG. 4 schematically represents the preparation of a fermented product containing yogurt ferments and ferments used in cheese manufacture;

FIG. 5 schematically represents the preparation of a fermented product of the set yogurt type.

MORE DETAILED DESCRIPTION

Figure 1:
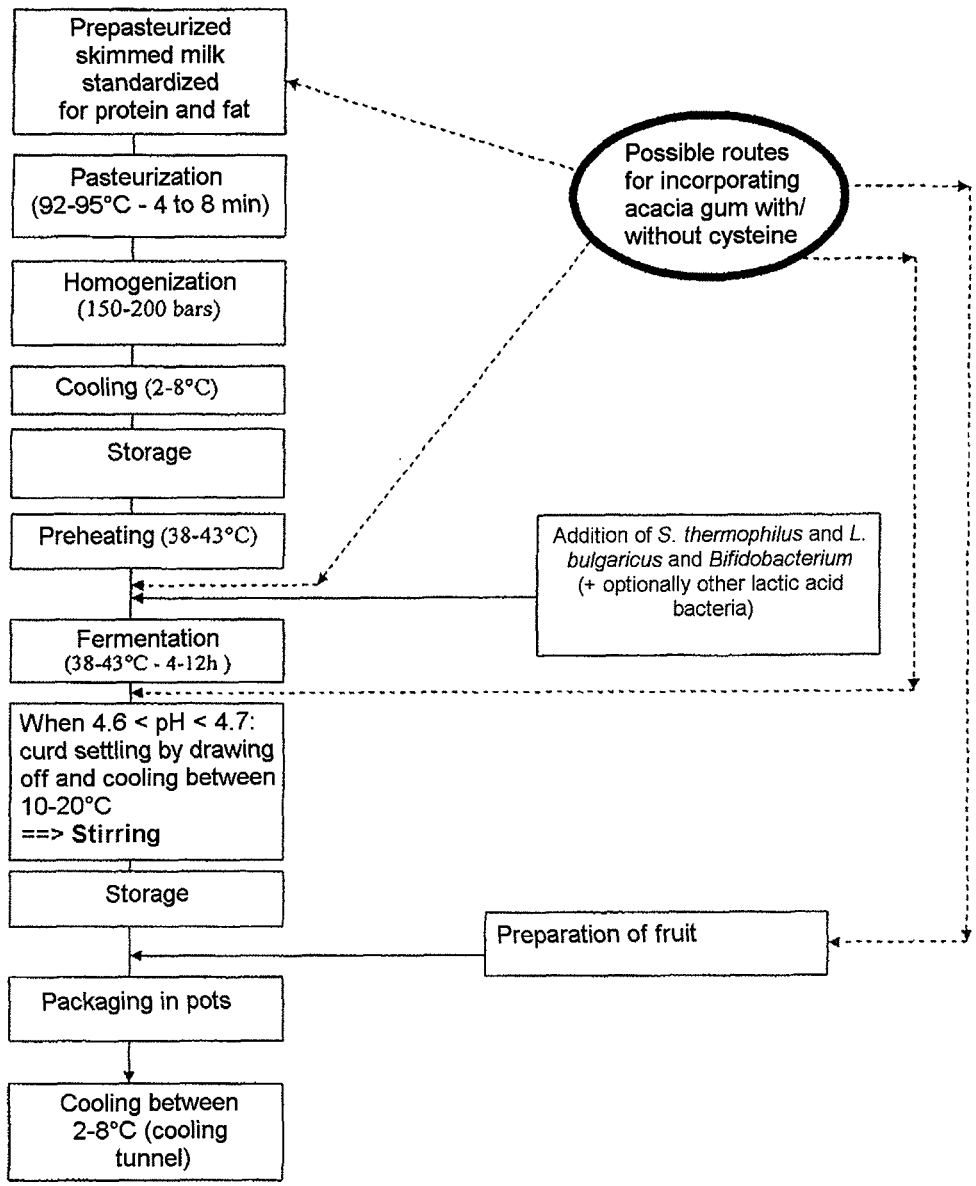
FIGS. 1 to 5 schematically represent, by way of non-limiting examples, the use of the method of the invention in the context of the preparation of various fermented dairy products.
Figure 2:
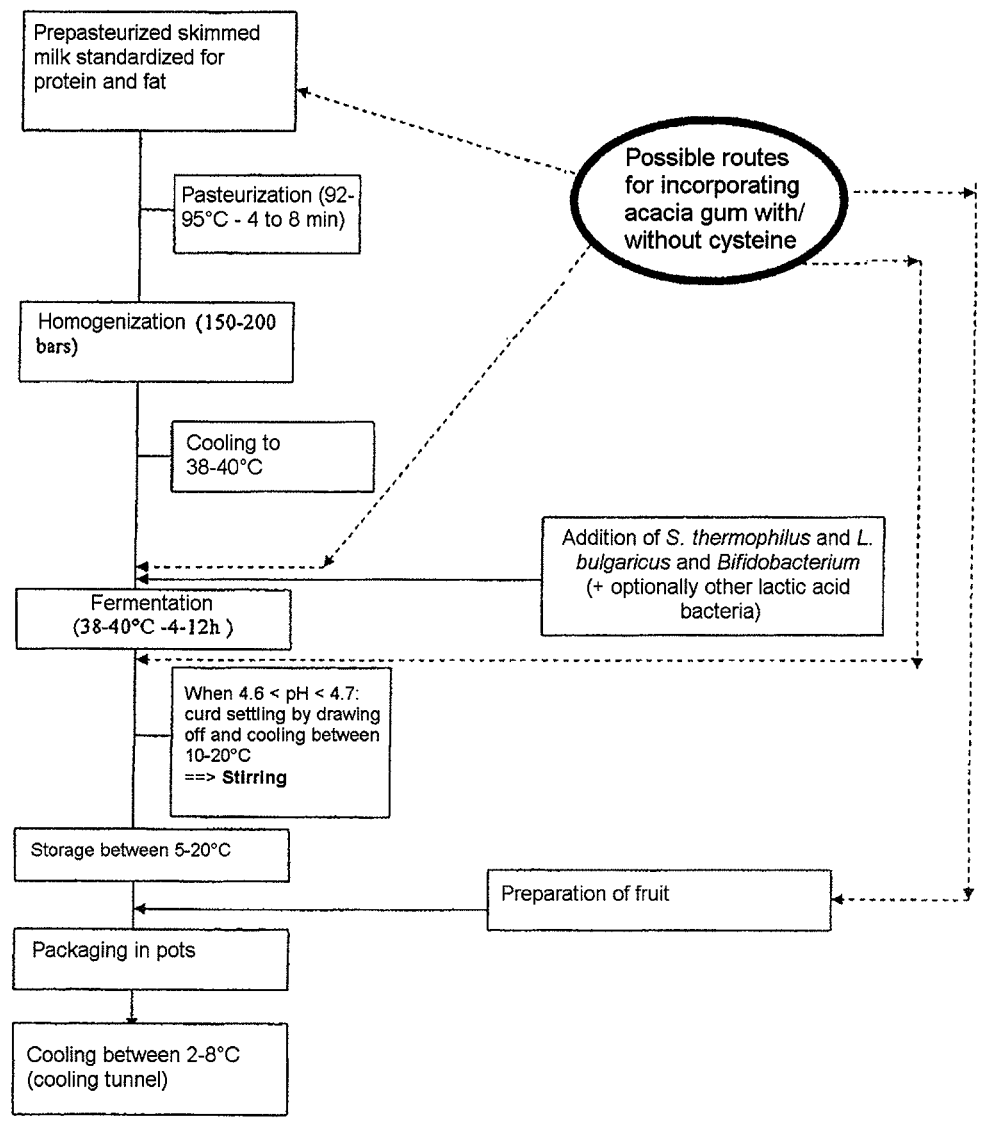
Figure 3:
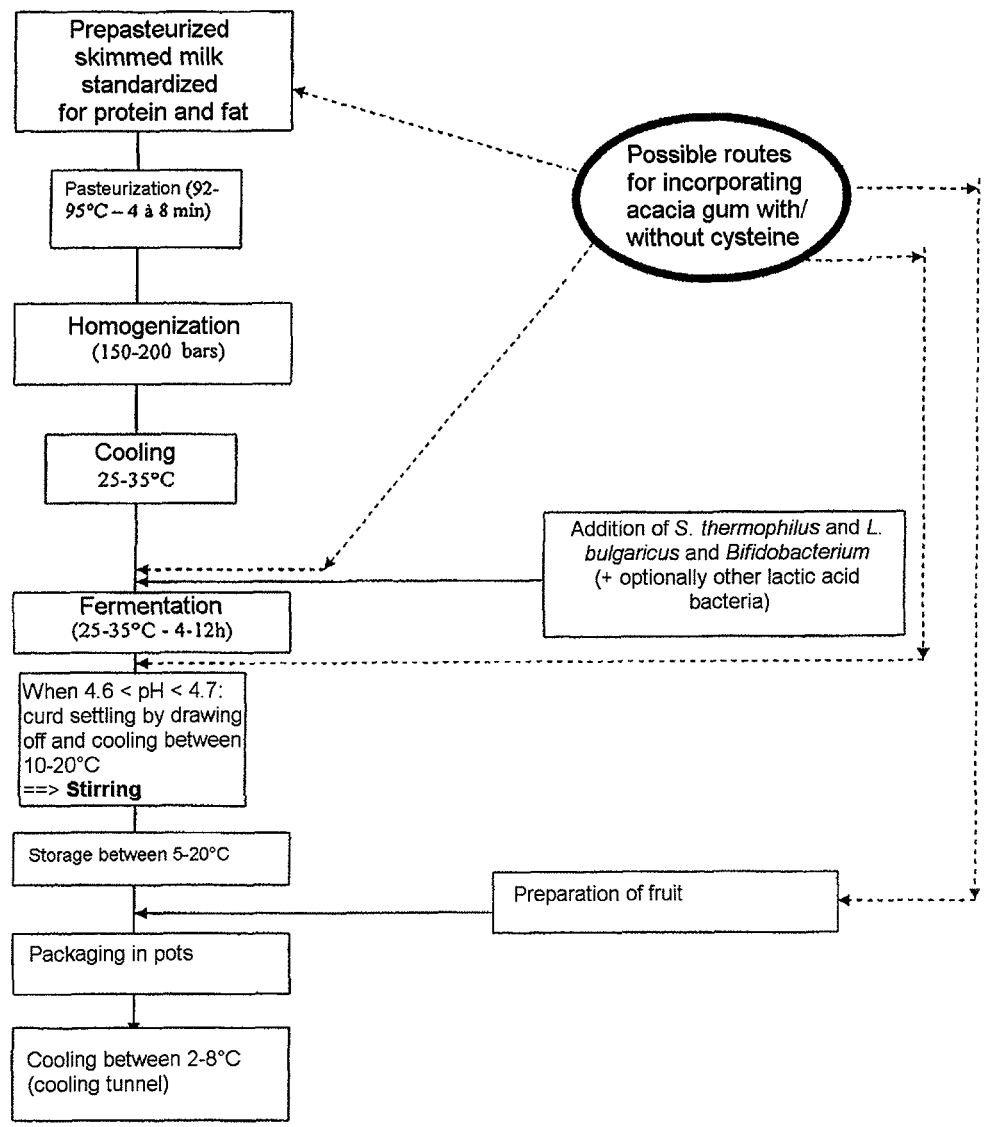
Figure 4:
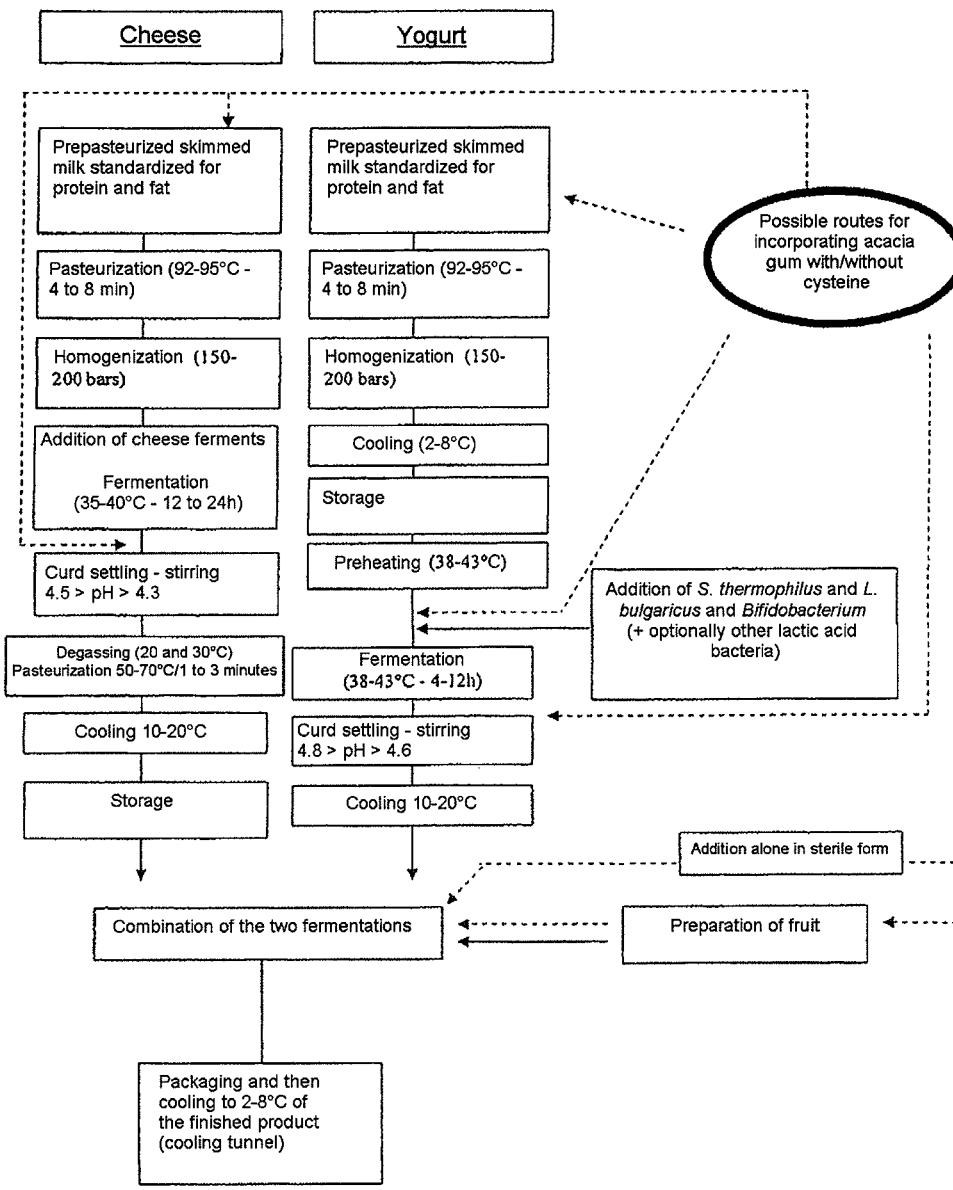
Figure 5:
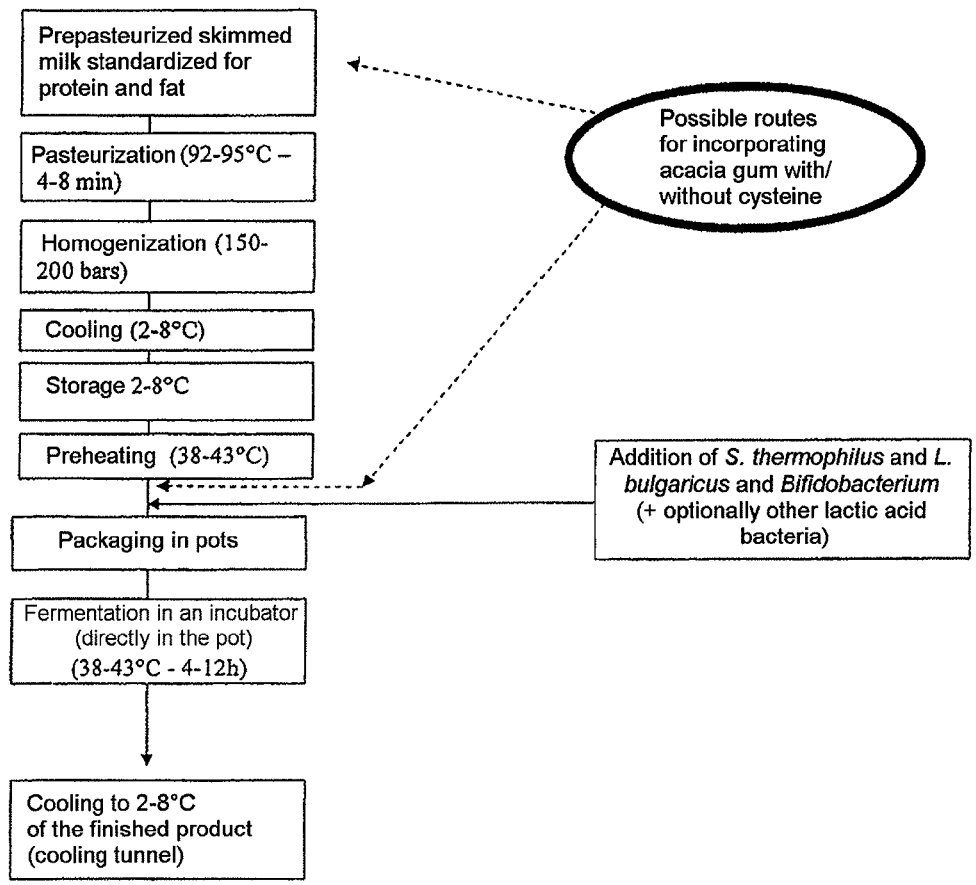

The subject of the present invention is also fermented food products, and in particular fermented dairy products and/or plant substrate-based products, which can be obtained by the method in accordance with the invention.

The subject of the present invention is also fermented food products provided in the form of fat-based fillings which can enter into the composition of cereal bars and cream biscuits.

Fermented food products in accordance with the invention contain from 0.1 to 3%, and preferably from 0.2 to 1% by weight of gum arabic, and advantageously also contain from about 5 to about 50 mg/l of sulfur-containing amino acid(s), preferably cysteine.

They also contain, immediately after fermentation and packaging, at least $1\times10^8$, preferably of the order of $2\times10^8$ to $10^9$ CFU of bifidobacteria per ml of product. Preferably after 28 days of preservation between 4 and 10° C., at least 40% of the bifidobacteria present at the end of the fermentation is still live in said products.

Particularly preferred products contain from 0.2 to 1% by weight of gum arabic, and from 5 to 10 mg/l of cysteine, and after 35 days of preservation between 4 and 10° C., at least 30% of the bifidobacteria present at the end of the fermentation is still live in said products. In a particularly preferred manner, the products are fermented dairy products, of the drinking yogurt type, containing from 2 to 3.5% of proteins.

The present invention will be understood more clearly with the aid of the additional description which follows, which refers to non-limiting examples illustrating the use of the method in accordance with the invention to stimulate the growth and increase the survival of bifidobacteria cultured in the presence of yogurt ferments.

EXAMPLE 1

Effect of *Acacia* Gum on the Growth and Survival of Bifidobacteria in a Dairy Product Experimental Protocol The formula chosen for the experimentation is a milk with a protein content of 4.4% and a fat content of 3.5%, obtained by reconstitution of milk powder. It is a formula which normally gives a low population of bifidobacteria.

Two doses of *acacia* gum (FIBREGUM® B) were studied: 0.5% and 1% by weight in the finished product. The *acacia* gum is incorporated during reconstitution. The reconstitution time is one hour.

The milk, supplemented with *acacia* gum, was heat-treated according to the following protocol:
preheating to 55° C.,
pasteurization at 95° C. for 6 minutes,
precooling to 40° C., cooling to 4° C.

The milk is then stored at 4° C. until it is used (within the next 24 hours).
Preparation for Inoculation:

40 minutes before inoculation, the milk is tempered at 38° C.

For the inoculation, the following inoculum is used:
*Streptococcus thermophilus*+*Lactobacillus delbrueckii* ssp. *Bulgaricus*+*Bifidobacterium animalis* ssp *lactis* (CNCM: I-2494), in an amount of $5\times10^6$ CFU/ml of *Streptococcus thermophilus*, $5\times10^6$ CFU/ml of *Lactobacillus bulgaricus* and $1\times10^7$ CFU/ml of *Bifidobacterium animalis*.

After inoculation, the milk is immersed again in the water bath at 38° C. The fermentation is monitored using the CINAC® system (YSEBAERT) until the curd settling pH is obtained (4.8).

Curd Settling, Smoothing, Packaging:

At pH=4.8, the fermented milk is smoothed and cooled to 20° C. (that is 6 liters/h) with a filter with a mesh of 500 μm. It is then packaged in 125 ml pots, and then placed in a cold tunnel (4° C.) overnight. The following morning, the pots are transferred to 10° C. and the microbiological monitoring is performed up to D28. The enumerations are performed in triplicate (3 measurements per trial) following the dicloxacillin method described by Grand et al., 2003.

Results

Figure 6:
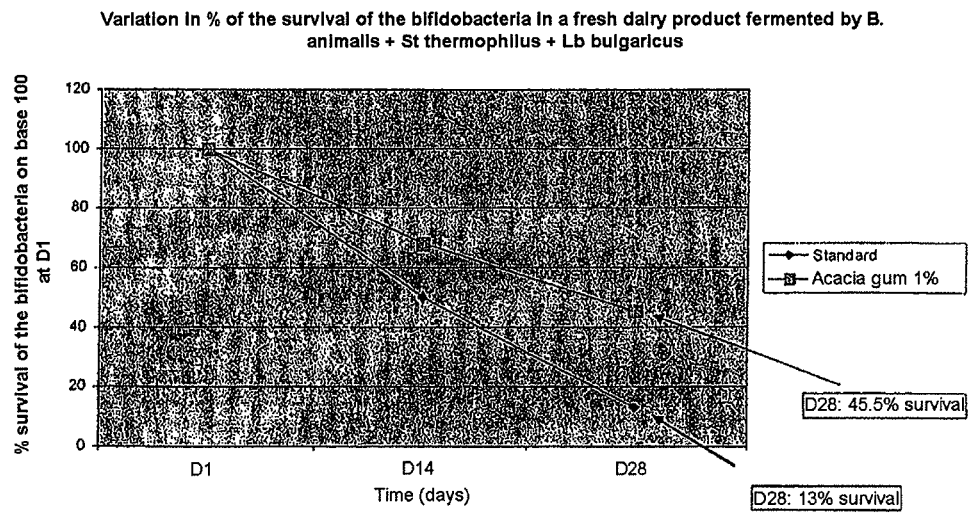
FIG. 6 Variation in % of the survival of the Bifidobacteria in a fresh dairy product fermented by *B. animalis*+*S. thermophilus*+*L. bulgaricus*

The results are illustrated by Table I, which indicates the populations of *Bifidobacterium animalis* at D1, D14 and D28, by Table II, which summarizes the percentage of survival at D14 and D28, and by FIG. 6 which represents the variation in % of the survival of bifidobacteria as a function of time.

TABLE I

|  | pop D 1 CFU/ml | pop D 14 CFU/ml | pop D 28 CFU/ml |
|---|---|---|---|
| Control | 2.30E+08 | 1.15E+08 | 3.00E+07 |
| Acacia 1% | 2.20E+08 | 1.50E+08 | 1.20E+08 |

TABLE II

|  | End fermentation D 1 | D +14 D 14 | D +28 D 28 |
|---|---|---|---|
| Control | 100 | 50 | 13 |
| Acacia gum 1% | 100 | 68 | 45.5 |

These results show clearly an improvement in the survival of the bacterial population at D+28 in the presence of 1% *acacia* gum (the populations at D+1 of the Control trial and of the *Acacia* trial not being statistically different).

At 0.5% of *acacia* gum, the effect is smaller (results not illustrated), but remains significant.

EXAMPLE 2

Effect of the Combination of *Acacia* Gum and Cysteine on the Growth and the Survival of Bifidobacteria in a Dairy Product Experimental Protocol A drinking yogurt (2.8% of proteins) is manufactured by reconstitution of milk powder, and supplemented with 0.8% (by weight) of *acacia* gum, as described in Example 1 above. This type of product is chosen for the trials since it is the one that poses the biggest problems in terms of maintaining the population of bifidobacteria during storage. The reconstituted milk, supplemented with *acacia* gum, is heat treated as described in Example 1 above, and homogenized (150-200 bar).

After cooling to 38-40° C., *Streptococcus thermophilus* and *Lactobacillus delbrueckii* ssp. *Bulgaricus* are added in an amount of $5\times10^6$ CFU/ml of *Streptococcus thermophilus*, $5\times10^6$ CFU/ml of *Lactobacillus bulgaricus*. *Bifidobacterium animalis* ssp *lactis* I-2494 is added in the form of a ferment for direct inoculation, such as those described in application FR 0606421 supplemented with cysteine or not. The supplemented ferment used corresponds to the addition of $1.92\times10^7$ CFU/ml of *Bifidobacterium animalis* and 6.9 mg/l of cysteine.

After inoculation, the fermentation is carried out at 38° C., and monitored using the CINAC® system (YSEBAERT) until the curd settling pH is obtained (4.3<pH<4.4).

The curd settling is obtained by drawing off and cooling between 10-20° C., and then stirring.

The product is then packaged in pots and then placed in a cold tunnel (4° C.).

The populations are then counted at 2 h of storage at 15° C., and then 2, 8 14, 28 and 37 days of storage at 10° C.

Results

Figure 7:
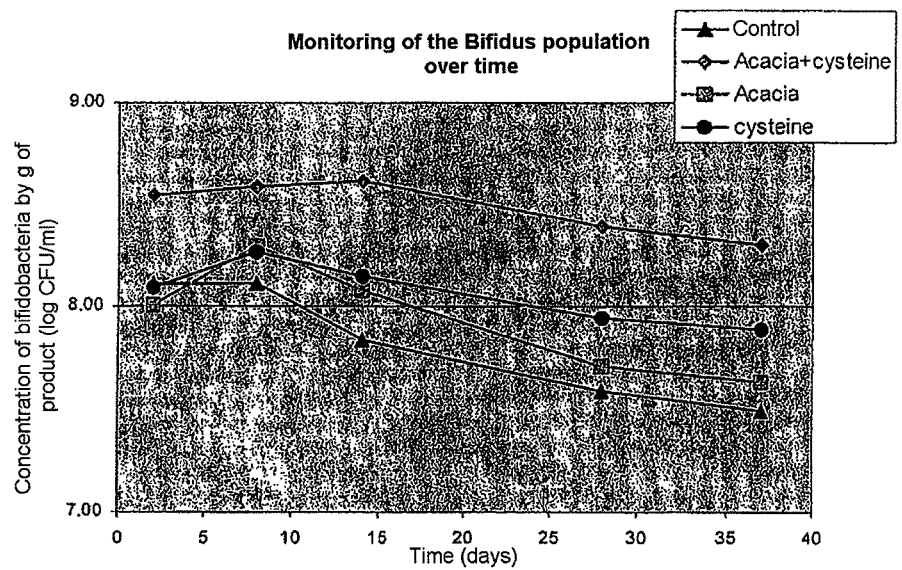
FIG. 7 Monitoring of Bifidus population over time

The results are illustrated by Table III below, and by FIG. 7, which represents the monitoring of the bifidobacteria population as a function of time.

These results show a very marked effect of *acacia* gum, and of the *acacia* gum+cysteine combination on the growth of the bifidobacteria. In the case of the *acacia* gum+cysteine combination, a particularly marked effect is additionally observed on the survival of the bifidobacteria during preservation.

TABLE III

|  | Trial 1 Acacia | Trial 2 Acacia + Cysteine | Control | Control Cysteine |
|---|---|---|---|---|
| Acacia gum | 0.8% | 0.8% | 0% | 0% |
| Pure equivalent of cysteine | 0 mg/l | 6.9 mg/l | 0 mg/l | 6.9 mg/l |
| Bifidus inoculated | 1.92E+7 CFU/g | 1.67E+7 CFU/g | 1.92E+7 CFU/g | 1.67E+7 CFU/g |
| Number of Bifidus at 2 h of storage | 2.3E+8 CFU/g | 5.4E+8 CFU/g | 1.3E+8 CFU/g | 2.1E+8 CFU/g |
| Number of Bifidus at D +2 | 1.0E+8 CFU/g | 3.5E+8 CFU/g | ND | 1.2E+8 CFU/g |
| Number of Bifidus at D +8 | 2E+8 CFU/g | 3.9E+8 CFU/g | 1.3E+8 CFU/g | 1.8E+8 CFU/g |
| Number of Bifidus at D +14 | 1.2E+8 CFU/g | 4.2E+8 CFU/g | 6.9E+7 CFU/g | 1.4E+8 CFU/g |
| Number of Bifidus at D +28 | 5.2E+7 CFU/g | 2.5E+8 CFU/g | 3.9E+7 CFU/g | 8.8E+7 CFU/g |
| Number of Bifidus at D +37 | 4.4E+7 CFU/g | 2.0E+8 CFU/g | 3.2E+7 CFU/g | 7.8E+7 CFU/g |

ND: not determined

The same experiment was repeated with a product containing 2.7% of proteins, containing 0.8% of *acacia* gum, and inoculated with a ferment supplemented with cysteine, corresponding to the addition of $1.90\times10^7$ CFU/ml of bifidobacteria *animalis* and 7 mg/l of cysteine.

The results are illustrated by Table IV.

These results confirm the effect of *acacia* gum, and especially of the *acacia* gum+cysteine combination on the survival of bifidobacteria. 52 days after inoculation, the surviving bifidobacteria are indeed twice as many in the product supplemented with *acacia* gum, and ten times as many in the product supplemented with *acacia* gum and cysteine as in the control product.

TABLE IV

|  | Trial 3 | Trial Cysteine | Trial Acacia | Control |
|---|---|---|---|---|
| Acacia gum | 0.8% | 0% | 0.8% | 0% |
| Pure equivalent of cysteine | 7 mg/l | 7 mg/l | 0 mg/l | 0 mg/l |
| Bifidus inoculated | 1.90E+07 CFU/g | 1.90E+07 CFU/g | 1.90E+07 CFU/g | 1.90E+07 CFU/g |
| Number of Bifidus at D +2 | 4.70E+08 CFU/g | 1.05E+08 CFU/g | 1.50E+08 CFU/g | 7.00E+07 CFU/g |
| Number of Bifidus at D +8 | 2.50E+08 CFU/g | 9.00E+07 CFU/g | 1.00E+08 CFU/g | 7.00E+07 CFU/g |
| Number of Bifidus at D +14 | 3.40E+08 CFU/g | 7.00E+07 CFU/g | 5.00E+07 CFU/g | 3.00E+07 CFU/g |
| Number of Bifidus at D +21 | 2.40E+08 CFU/g | 4.00E+07 CFU/g | 6.00E+07 CFU/g | 3.00E+07 CFU/g |
| Number of Bifidus at D +28 | 1.20E+08 CFU/g | 2.00E+07 CFU/g | 3.00E+07 CFU/g | 9.00E+06 CFU/g |
| Number of Bifidus at D +35 | 1.00E+08 CFU/g | 6.00E+06 CFU/g | 1.00E+07 CFU/g | 5.00E+06 CFU/g |
| Number of Bifidus at D +52 | 3.00E+07 CFU/g | 3.00E+06 CFU/g | 6.00E+06 CFU/g | 3.00E+06 CFU/g |

BIBLIOGRAPHIC REFERENCES

Lian et al.; Survival of Bifidobacteria after spray-drying. International Journal of Food Microbiology, 2002, vol. 74, No. 1/2, p. 79-86.

Lian et al.; Viability of microencapsulated bifidobacteria in simulated gastric juice and bile solution. International Journal of Food Microbiology, 2003, vol. 86, No. 3, p. 293-301.

Hsiao et al. 2004; Effect of packaging conditions and temperature on viability of microencapsulated bifidobacteria during storage. Journal of Science of Food and Agriculture, 2004, vol. 84, No. 2, p. 134-139.

Desmond et al. 2002. Improved survival of *Lactobacillus paracasei* NFBC 338 in spray-dried powders containing gum *acacia*. Journal of Applied Microbiology, 2002, vol. 93, p. 1003-1011.

Wyatt et al. 1986; A change in human faecal flora in response to inclusion of gum arabic in the diet. British Journal of Nutrition, 1986, vol. 55, No. 2, p. 261-266.

Cherbut et al. 2003; *Acacia* gum in a bifidogenic dietary fibre with high digestive tolerance in healthy humans. Microbial Ecology in Health and Disease, 2003, vol. 15, No. 1, p. 43-50.

Grand et al., 2003; Quantitative analysis and molecular identification of bifidobacteria strains in probiotic milk products. European Food Research and Technology, vol. 217, p. 90-92.

The invention claimed is:

1. A method of preparing a fermented fresh food product wherein said method comprises a step of fermenting an appropriate food substrate by a ferment comprising one or more strains of *Bifidobacterium animalis*, wherein said method comprises the addition of gum Arabic to said food product before packaging of said food product, and wherein the final concentration of gum Arabic in said food product is from about 0.1 to about 3% by weight.

2. The method as claimed in claim 1, wherein said ferment additionally contains one or more strains of lactic acid bacteria other than *Bifidobacterium*.

3. The method as claimed in claim 1, wherein said method additionally comprises the addition of at least one sulfur-containing amino acid to said food product before its packaging.

4. The method as claimed in claim 3, wherein said sulfur-containing amino acid is cysteine.

5. The method as claimed in claim 3, wherein the sulfur-containing amino acid(s) is (are) added so that its (their) final concentration is about 5 to about 50 mg/l.

6. The method as claimed in claim 3, wherein a portion of the final quantity of gum Arabic, and optionally a portion of the final quantity of sulfur-containing amino acid, is added before the fermentation step, and the remaining portion of the final quantity of gum Arabic, and optionally the remaining portion of the final quantity of sulfur-containing amino acid is added after said fermentation step.

7. The method as claimed in claim 2, wherein the lactic acid bacteria other than *Bifidobacterium* comprise one or more *Streptococcus thermophilus* strains and one or more *Lactobacillus delbrueckii* subsp. *bulgaricus* strains.

8. A fermented food product which can be obtained by a method as claimed in claim 1.

9. The fermented food product as claimed in claim 8, which is a fermented dairy product.

10. The fermented food product as claimed in claim 8, which is a product based on a fermented plant substrate.

11. The fermented food product as claimed in claim 8, which is a fat-based filling.

12. The method as claimed in claim 3, wherein the gum Arabic, and optionally the sulfur-containing amino acid, is added before the fermentation step.

13. A method of preparing a fermented fresh food product wherein said method comprises a step of fermenting an appropriate food substrate by a ferment comprising one or more strains of *Bifidobacterium animalis*, wherein said method comprises the addition of gum Arabic to said food product before packaging of said food product, and wherein the final concentration of gum Arabic in said food product is from about 0.1 to about 3% by weight, and wherein said method additionally comprises the addition of at least one sulfur-containing amino acid to said food product before its packaging.

* * * * *